US012670587B2

(12) United States Patent  
Ceroici et al.

(10) Patent No.: US 12,670,587 B2  
(45) Date of Patent: Jun. 30, 2026

(54) AUTOMATIC ANNOTATION OF CONDITION FEATURES IN MEDICAL IMAGES

(71) Applicant: Pulsemedica Corp., Edmonton (CA)

(72) Inventors: Christopher Ceroici, Edmonton (CA); Nir Katchinskiy, Edmonton (CA)

(73) Assignee: PulseMedica Corp., Edmonton (CA)

( * ) Notice: Subject to any disclaimer, the term of this patent is extended or adjusted under 35 U.S.C. 154(b) by 208 days.

(21) Appl. No.: 18/257,797

(22) PCT Filed: Dec. 21, 2021

(86) PCT No.: PCT/CA2021/051853  
§ 371 (c)(1),  
(2) Date: Jun. 15, 2023

(87) PCT Pub. No.: WO2022/133590  
PCT Pub. Date: Jun. 30, 2022

(65) Prior Publication Data  
US 2024/0054638 A1 Feb. 15, 2024

(30) Foreign Application Priority Data

Dec. 23, 2020 (CA) ...................................... 3103872

(51) Int. Cl.  
*G06T 7/00* (2017.01)  
*G06N 20/00* (2019.01)  
(Continued)

(52) U.S. Cl.  
CPC ........... *G06T 7/0012* (2013.01); *G06N 20/00* (2019.01); *G06V 10/25* (2022.01); *G06V 10/462* (2022.01);  
(Continued)

(58) Field of Classification Search  
CPC .............. G06T 7/0012; G06T 2200/24; G06T 2207/20081; G06T 2207/20101;  
(Continued)

(56) References Cited

U.S. PATENT DOCUMENTS

| | | | |
|---|---|---|---|
| 5,590,653 A | 1/1997 | Aida et al. | |
| 5,975,697 A | 11/1999 | Podoleanu et al. | |

(Continued)

FOREIGN PATENT DOCUMENTS

| | | |
|---|---|---|
| BR | 112019005675 A2 | 6/2019 |
| CA | 2714116 A1 | 8/2009 |

(Continued)

OTHER PUBLICATIONS

Patent Cooperation Treaty, International Search Report for International Application No. PCT/CA2021/051853, Mar. 22, 2022, 4 pages.

(Continued)

*Primary Examiner* — Ping Y Hsieh  
*Assistant Examiner* — Jose M Torres  
(74) *Attorney, Agent, or Firm* — Perkins Coie LLP

(57) ABSTRACT

Features of a medical condition can be automatically annotated in medical images using a classification model that has been trained to classify images as having the medical condition or not. The automatically annotated features may be further processed to generate a treatment plan for treating the medical condition, for example with a laser, ultrasound, or other treatment method.

17 Claims, 8 Drawing Sheets

(51) Int. Cl.

| | |
|---|---|
| *G06V 10/25* | (2022.01) |
| *G06V 10/46* | (2022.01) |
| *G06V 10/764* | (2022.01) |
| *G06V 10/774* | (2022.01) |
| *G06V 10/94* | (2022.01) |
| *G06V 40/14* | (2022.01) |
| *G16H 30/40* | (2018.01) |

(52) U.S. Cl.
CPC .......... *G06V 10/764* (2022.01); *G06V 10/774* (2022.01); *G06V 10/945* (2022.01); *G06V 40/14* (2022.01); *G16H 30/40* (2018.01); *G06T 2200/24* (2013.01); *G06T 2207/20081* (2013.01); *G06T 2207/20101* (2013.01); *G06V 2201/03* (2022.01)

(58) Field of Classification Search
CPC .... G06V 10/25; G06V 10/462; G06V 10/764; G06V 10/774; G06V 10/945; G06V 40/14; G06V 2201/03; G16H 30/40; G01T 1/2992; G06N 20/00
See application file for complete search history.

(56) References Cited

U.S. PATENT DOCUMENTS

| | | | |
|---|---|---|---|
| 6,789,900 B2 | 9/2004 | Van de Velde | |
| 7,639,847 B2 | 12/2009 | Middleton et al. | |
| 7,805,009 B2 | 9/2010 | Everett et al. | |
| 7,980,696 B1 | 7/2011 | Taki et al. | |
| 9,550,069 B1 | 1/2017 | Elezzabi | |
| 9,675,243 B2 | 6/2017 | Sasaki et al. | |
| 10,117,576 B2 | 11/2018 | De et al. | |
| 10,599,984 B1 * | 3/2020 | Wubbels | G16H 50/20 |
| 10,636,146 B2 | 4/2020 | Zhong et al. | |
| 10,694,939 B2 | 6/2020 | Kuo et al. | |
| 11,617,509 B2 | 4/2023 | Anderson et al. | |
| 11,776,093 B2 | 10/2023 | Woodard et al. | |
| 11,922,627 B2 | 3/2024 | Min et al. | |
| 11,992,440 B2 | 5/2024 | Katchinskiy et al. | |
| 11,998,487 B2 | 6/2024 | Katchinskiy et al. | |
| 12,051,202 B2 | 7/2024 | Freiman et al. | |
| 12,138,026 B2 | 11/2024 | Grady et al. | |
| 12,141,975 B2 | 11/2024 | Buckler et al. | |
| 12,142,384 B2 | 11/2024 | Rabbat et al. | |
| 12,144,669 B2 | 11/2024 | Min | |
| 12,150,788 B2 | 11/2024 | Forneris et al. | |
| 12,154,321 B2 | 11/2024 | Phillips et al. | |
| 12,159,406 B2 | 12/2024 | Buckler et al. | |
| 12,178,557 B2 | 12/2024 | Grady et al. | |
| 12,186,062 B2 | 1/2025 | Fonte et al. | |
| 12,223,093 B2 | 2/2025 | Yousfi et al. | |
| 12,223,649 B2 | 2/2025 | Grady et al. | |
| 12,229,957 B2 | 2/2025 | Buckler et al. | |
| 12,236,595 B2 | 2/2025 | Buckler et al. | |
| 12,245,971 B2 | 3/2025 | Katchinskiy et al. | |
| 12,303,432 B2 | 5/2025 | Katchinskiy et al. | |
| 12,343,289 B2 | 7/2025 | Katchinskiy et al. | |
| 2003/0120325 A1 | 6/2003 | Fujisaka et al. | |
| 2004/0174495 A1 | 9/2004 | Levine | |
| 2004/0254567 A1 | 12/2004 | Holz et al. | |
| 2007/0046948 A1 | 3/2007 | Podoleanu et al. | |
| 2007/0115481 A1 | 5/2007 | Toth et al. | |
| 2008/0015553 A1 | 1/2008 | Zacharias | |
| 2008/0242977 A1 | 10/2008 | Sirohey et al. | |
| 2009/0093798 A1 | 4/2009 | Charles | |
| 2009/0103794 A1 * | 4/2009 | Sathyanarayana | G06T 7/0012 |
| | | | 382/224 |
| 2009/0131921 A1 | 5/2009 | Kurtz et al. | |
| 2009/0171250 A1 | 7/2009 | Rybyanets | |
| 2009/0182312 A1 | 7/2009 | Gertner et al. | |
| 2010/0094135 A1 | 4/2010 | Fang-Yen et al. | |
| 2010/0182610 A1 | 7/2010 | Utsunomiya | |
| 2010/0290007 A1 | 11/2010 | Van De Velde | |

| | | | |
|---|---|---|---|
| 2011/0009779 A1 | 1/2011 | Romano et al. | |
| 2011/0028894 A1 | 2/2011 | Foley et al. | |
| 2011/0043661 A1 | 2/2011 | Podoleanu | |
| 2011/0058175 A1 | 3/2011 | Suehira | |
| 2011/0134436 A1 | 6/2011 | Podoleanu et al. | |
| 2011/0234978 A1 | 9/2011 | Hammer et al. | |
| 2011/0301508 A1 | 12/2011 | Sethuraman et al. | |
| 2012/0002164 A1 | 1/2012 | Yamamoto et al. | |
| 2012/0008838 A1 * | 1/2012 | Guyon | G16H 50/20 |
| | | | 382/128 |
| 2012/0041318 A1 | 2/2012 | Taylor | |
| 2012/0041739 A1 | 2/2012 | Taylor | |
| 2012/0154747 A1 | 6/2012 | Makihira | |
| 2012/0165799 A1 | 6/2012 | Yamamoto | |
| 2012/0274904 A1 | 11/2012 | Saito et al. | |
| 2012/0294500 A1 | 11/2012 | Utsunomiya et al. | |
| 2013/0012380 A1 | 1/2013 | Le et al. | |
| 2013/0172713 A1 | 7/2013 | Kirschenman | |
| 2013/0274725 A1 | 10/2013 | Rathjen et al. | |
| 2013/0286348 A1 | 10/2013 | Makihira et al. | |
| 2013/0327244 A1 | 12/2013 | Robbert et al. | |
| 2014/0104618 A1 | 4/2014 | Potsaid et al. | |
| 2014/0194860 A1 | 7/2014 | Dick et al. | |
| 2014/0221810 A1 | 8/2014 | Kacprowicz | |
| 2014/0243662 A1 | 8/2014 | Mittal et al. | |
| 2014/0324029 A1 | 10/2014 | Rathjen | |
| 2015/0116664 A1 | 4/2015 | Uchida | |
| 2015/0141972 A1 | 5/2015 | Woodley et al. | |
| 2015/0272448 A1 | 10/2015 | Fonte et al. | |
| 2015/0305617 A1 | 10/2015 | Tachikawa et al. | |
| 2016/0022490 A1 | 1/2016 | Ergun et al. | |
| 2016/0074221 A1 | 3/2016 | Tassignon et al. | |
| 2016/0224753 A1 | 8/2016 | Grady et al. | |
| 2016/0250067 A1 | 9/2016 | Iwata et al. | |
| 2016/0284103 A1 | 9/2016 | Huang | |
| 2017/0007112 A1 | 1/2017 | Gonzalez | |
| 2017/0035291 A1 | 2/2017 | Jiao et al. | |
| 2017/0098301 A1 * | 4/2017 | Ikemoto | G06T 7/0012 |
| 2017/0132826 A1 | 5/2017 | Grady et al. | |
| 2017/0165456 A1 | 6/2017 | Tutungi et al. | |
| 2017/0188822 A1 | 7/2017 | Yang | |
| 2017/0189228 A1 | 7/2017 | Yang et al. | |
| 2017/0224305 A1 | 8/2017 | Ho et al. | |
| 2017/0238798 A1 | 8/2017 | Isogai et al. | |
| 2017/0252213 A1 | 9/2017 | Furuuchi et al. | |
| 2017/0310901 A1 | 10/2017 | Sheikh et al. | |
| 2017/0340483 A1 | 11/2017 | Rill et al. | |
| 2017/0360411 A1 | 12/2017 | Rothberg et al. | |
| 2018/0101644 A1 | 4/2018 | Hammes et al. | |
| 2018/0111008 A1 | 4/2018 | Chapuis et al. | |
| 2018/0116502 A1 | 5/2018 | Ishinabe | |
| 2018/0200112 A1 | 7/2018 | Krampert et al. | |
| 2018/0207029 A1 | 7/2018 | Herekar et al. | |
| 2018/0253531 A1 | 9/2018 | Sharma et al. | |
| 2018/0271362 A1 | 9/2018 | Palczewski et al. | |
| 2018/0344150 A1 | 12/2018 | Bajraszewski et al. | |
| 2018/0353064 A1 | 12/2018 | Soetikno et al. | |
| 2019/0000316 A1 | 1/2019 | Hirose et al. | |
| 2019/0000568 A1 | 1/2019 | Connolly et al. | |
| 2019/0038766 A1 | 2/2019 | Mohanty et al. | |
| 2019/0083060 A1 | 3/2019 | Ho et al. | |
| 2019/0099291 A1 | 4/2019 | Herekar et al. | |
| 2019/0105519 A1 | 4/2019 | Herekar et al. | |
| 2019/0114804 A1 | 4/2019 | Sundaresan et al. | |
| 2019/0125178 A1 | 5/2019 | Murata | |
| 2019/0130580 A1 | 5/2019 | Chen et al. | |
| 2019/0150869 A1 | 5/2019 | Passerini et al. | |
| 2019/0188851 A1 | 6/2019 | Zouridakis | |
| 2019/0223809 A1 | 7/2019 | Daughton et al. | |
| 2019/0278972 A1 | 9/2019 | Anderson et al. | |
| 2019/0314194 A1 | 10/2019 | Artsyukhovich et al. | |
| 2019/0332900 A1 * | 10/2019 | Sjolund | G06T 9/002 |
| 2019/0339356 A1 | 11/2019 | Schildknecht et al. | |
| 2019/0358065 A1 | 11/2019 | Grady et al. | |
| 2019/0388274 A1 | 12/2019 | Claus et al. | |
| 2020/0015675 A1 | 1/2020 | Shibutani et al. | |
| 2020/0160301 A1 | 5/2020 | Lyman et al. | |
| 2020/0194108 A1 | 6/2020 | Podilchuk et al. | |
| 2020/0211694 A1 * | 7/2020 | Nye | G06T 7/11 |

(56) References Cited

U.S. PATENT DOCUMENTS

| | | | |
|---|---|---|---|
| 2020/0218943 A1 | 7/2020 | Osake | |
| 2020/0242768 A1 | 7/2020 | Ashok et al. | |
| 2020/0245960 A1 | 8/2020 | Richter et al. | |
| 2020/0250436 A1 | 8/2020 | Lee et al. | |
| 2020/0250814 A1* | 8/2020 | Stoval, III | G06N 3/04 |
| 2020/0265276 A1* | 8/2020 | Xu | G06V 10/454 |
| 2020/0273559 A1 | 8/2020 | Yousfi et al. | |
| 2020/0285906 A1 | 9/2020 | Do et al. | |
| 2020/0288973 A1 | 9/2020 | Ono | |
| 2020/0294654 A1 | 9/2020 | Harzig et al. | |
| 2020/0320692 A1* | 10/2020 | Fleming | G06T 7/0012 |
| 2020/0349434 A1* | 11/2020 | Zhang | G06N 3/042 |
| 2020/0352785 A1 | 11/2020 | Holland et al. | |
| 2020/0360088 A1 | 11/2020 | Sankaran et al. | |
| 2020/0380675 A1* | 12/2020 | Golden | G06T 7/0012 |
| 2020/0407013 A1 | 12/2020 | Corbett et al. | |
| 2021/0022705 A1 | 1/2021 | Suzuki et al. | |
| 2021/0045672 A1 | 2/2021 | Jia et al. | |
| 2021/0056684 A1* | 2/2021 | Zhou | G06V 10/82 |
| 2021/0056696 A1 | 2/2021 | Bronkalla et al. | |
| 2021/0142487 A1 | 5/2021 | Xu et al. | |
| 2021/0158541 A1 | 5/2021 | Figueroa-Alvarez et al. | |
| 2021/0186753 A1 | 6/2021 | Al-Qaisi et al. | |
| 2021/0202062 A1 | 7/2021 | Gray et al. | |
| 2021/0202072 A1 | 7/2021 | Yi et al. | |
| 2021/0224997 A1 | 7/2021 | Kushida et al. | |
| 2021/0253138 A1 | 8/2021 | Neumaier et al. | |
| 2021/0295528 A1* | 9/2021 | Fuchs | G06V 10/751 |
| 2021/0338088 A1 | 11/2021 | Bouwman et al. | |
| 2021/0383262 A1* | 12/2021 | Elen | G06F 18/2163 |
| 2021/0404655 A1* | 12/2021 | Bijkerk | F23D 14/02 |
| 2022/0079540 A1 | 3/2022 | Sankaran et al. | |
| 2022/0117780 A1 | 4/2022 | Zhang | |
| 2022/0139005 A1 | 5/2022 | Antoniades et al. | |
| 2022/0151483 A1 | 5/2022 | Ono et al. | |
| 2022/0180512 A1* | 6/2022 | Oh | G06T 7/30 |
| 2022/0230312 A1 | 7/2022 | Choi et al. | |
| 2022/0287878 A1 | 9/2022 | Herekar et al. | |
| 2022/0390369 A1 | 12/2022 | Piestun et al. | |
| 2022/0398706 A1 | 12/2022 | Buckler et al. | |
| 2023/0089026 A1* | 3/2023 | Tran | A61B 6/48 |
| | | | 705/2 |
| 2023/0103319 A1 | 4/2023 | Monajemi et al. | |
| 2023/0202533 A1 | 6/2023 | Nativ | |
| 2023/0245772 A1* | 8/2023 | Fang | G06T 7/0012 |
| | | | 705/2 |
| 2023/0260111 A1* | 8/2023 | Rodrigues-Diaz | G06T 7/0012 |
| | | | 382/128 |
| 2023/0326127 A1 | 10/2023 | Zhong et al. | |
| 2023/0372153 A1 | 11/2023 | Katchinskiy et al. | |
| 2023/0381022 A1 | 11/2023 | Katchinskiy et al. | |
| 2023/0386026 A1 | 11/2023 | Buckler | |
| 2023/0397816 A1 | 12/2023 | Forneris et al. | |
| 2024/0016660 A1 | 1/2024 | Katchinskiy et al. | |
| 2024/0020830 A1* | 1/2024 | Diaz | G16H 50/70 |
| 2024/0115423 A1 | 4/2024 | Katchinskiy et al. | |
| 2024/0259352 A1 | 8/2024 | Yousfi et al. | |
| 2024/0269001 A1 | 8/2024 | Katchinskiy et al. | |
| 2024/0366427 A1 | 11/2024 | Katchinskiy et al. | |
| 2024/0366429 A1 | 11/2024 | Katchinskiy et al. | |
| 2024/0371000 A1 | 11/2024 | Buckler | |
| 2024/0386652 A1 | 11/2024 | Grady et al. | |
| 2024/0387045 A1 | 11/2024 | Lynch et al. | |
| 2024/0394841 A1 | 11/2024 | Buckler et al. | |
| 2024/0407849 A1 | 12/2024 | Sankaran et al. | |
| 2024/0407950 A1 | 12/2024 | Katchinskiy et al. | |
| 2024/0428424 A1 | 12/2024 | Grady et al. | |
| 2024/0428561 A1 | 12/2024 | Katchinskiy et al. | |
| 2025/0005744 A1 | 1/2025 | Ihdayhid et al. | |
| 2025/0025061 A1 | 1/2025 | Grady et al. | |
| 2025/0037437 A1 | 1/2025 | Phillips et al. | |
| 2025/0045457 A1 | 2/2025 | Yi et al. | |
| 2025/0049408 A1 | 2/2025 | Flack et al. | |
| 2025/0049591 A1 | 2/2025 | Wodlinger et al. | |
| 2025/0054143 A1 | 2/2025 | Yu et al. | |
| 2025/0061572 A1 | 2/2025 | Buckler et al. | |
| 2025/0079020 A1 | 3/2025 | Forneris et al. | |
| 2025/0082218 A1 | 3/2025 | Fonte et al. | |
| 2025/0090034 A1 | 3/2025 | Grady et al. | |
| 2025/0127535 A1 | 4/2025 | Katchinskiy et al. | |
| 2025/0161112 A1 | 5/2025 | Katchinskiy et al. | |
| 2025/0255477 A1 | 8/2025 | Katchinskiy et al. | |
| 2025/0262091 A1 | 8/2025 | Katchinskiy et al. | |
| 2025/0299468 A1 | 9/2025 | Katchinskiy et al. | |

FOREIGN PATENT DOCUMENTS

| | | | | |
|---|---|---|---|---|
| CA | 3096285 A1 | 4/2022 | | |
| CA | 3157811 A1 | 11/2023 | | |
| CN | 109561989 A | 4/2019 | | |
| CN | 109938919 A | 6/2019 | | |
| CN | 110176297 A | 8/2019 | | |
| CN | 113440112 A | 9/2021 | | |
| CN | 114511738 A | 5/2022 | | |
| CN | 117788881 A | 3/2024 | | |
| CN | 119851269 A | 4/2025 | | |
| EP | 1401326 A2 | 3/2004 | | |
| EP | 2403603 B1 | 7/2014 | | |
| EP | 4288973 A1 | 12/2023 | | |
| EP | 3033010 B1 | 1/2025 | | |
| EP | 4498327 A1 | 1/2025 | | |
| EP | 4220663 B1 | 2/2025 | | |
| EP | 4510140 A1 | 2/2025 | | |
| EP | 4490670 A4 | 4/2025 | | |
| FR | 3121535 A1 | 10/2022 | | |
| HK | 40108984 | 11/2024 | | |
| JP | 2001-299941 A | 10/2001 | | |
| JP | 2003-339758 A | 12/2003 | | |
| JP | 2008-289861 A | 12/2008 | | |
| JP | 2013-165874 A | 8/2013 | | |
| JP | 2015-195923 A | 11/2015 | | |
| JP | 2017-516604 A | 6/2017 | | |
| JP | 2017-184874 A | 10/2017 | | |
| JP | 2018-509975 A | 4/2018 | | |
| JP | 2022-520869 A | 4/2022 | | |
| JP | 2022-520987 A | 4/2022 | | |
| JP | 2022-533345 A | 7/2022 | | |
| JP | 2023-112190 A | 8/2023 | | |
| JP | 7590499 B2 | 11/2024 | | |
| JP | 7594538 B2 | 12/2024 | | |
| JP | 7603014 B2 | 12/2024 | | |
| JP | 7616806 B2 | 1/2025 | | |
| JP | 7631404 B2 | 2/2025 | | |
| JP | 7657945 B2 | 4/2025 | | |
| KR | 10-2019-0130310 A | 11/2019 | | |
| KR | 10-2731898 B1 | 11/2024 | | |
| KR | 10-2025-0017458 A | 2/2025 | | |
| KR | 10-2025-0024143 A | 2/2025 | | |
| MX | 388472 B | 3/2025 | | |
| WO | 94/24946 A1 | 11/1994 | | |
| WO | 2016/011045 A1 | 1/2016 | | |
| WO | 2019/231844 A1 | 12/2019 | | |
| WO | 2020/012841 A1 | 1/2020 | | |
| WO | 2020020809 A1 | 1/2020 | | |
| WO | 2020/058459 A1 | 3/2020 | | |
| WO | 2020/105228 A1 | 5/2020 | | |
| WO | WO-2020176039 A1 * | 9/2020 | | G06V 40/197 |
| WO | 2020/215359 A1 | 10/2020 | | |
| WO | 2020227661 A1 | 11/2020 | | |
| WO | 2021/029231 A1 | 2/2021 | | |
| WO | 2021/069168 A1 | 4/2021 | | |
| WO | 2021/069220 A1 | 4/2021 | | |
| WO | 2021/122762 A1 | 6/2021 | | |
| WO | 2022/077117 A1 | 4/2022 | | |
| WO | 2022/133590 A1 | 6/2022 | | |
| WO | 2023/065042 A1 | 4/2023 | | |
| WO | 2023/172273 A1 | 9/2023 | | |

(56)                    References Cited

FOREIGN PATENT DOCUMENTS

WO          2023/212825 A1      11/2023
WO          2024/238786 A1      11/2024

OTHER PUBLICATIONS

Gomez, A., et al., "Image Reconstruction in a Manifold of Image Patches: Application to Whole-Fetus Ultrasound Imaging", Machine Learning for Medical Image Reconstruction, Oct. 24, 2019, pp. 226-235.

Kaplan, S., et al., "Contrastive Learning for Generating Optical Coherence Tomography Images of the Retina"; Simulation and Synthesis in Medical Imaging, Sep. 21, 2022, pp. 112-121.

Tam, Johnny and Yang, Qiang; "Optics Retinal Imaging with Eye Tracking"; found at: Adaptive Optics Retinal Imaging with Eye Tracking, National Institute of Biomedical Imaging and Bioengineering (nib.gov) Retrieved: Jan. 16, 2025.

Clarivate Analytics, Translation of CN-110176297-A (Year: 2025).

Ebbini, Emad S., and Charles A. Cain. "Aspherical-section ultrasound phased array applicator for deep localized hyperthermia." IEEE Transactions on Biomedical Engineering 38.7 (1991): 634-643.

Gombar et al. 2007 Indian Journal of Anaesthesia 51:287-302 (Year: 2007).

Kirkeeide, R. L., et al., "Assessment of coronary stenoses by myocardial perfusion imaging during pharmacologic coronary vasodilation. VII. Validation of coronary flow reserve as a single integrated functional measure of stenosis severity reflecting all its geometric dimensions", Journal of the American College of Cardiology, vol. 7, No. 1, Jan. 1986, pp. 103-113.

Kitabata, H., et al., "Coronary Microvascular Resistance Index Immediately After Primary Percutaneous Coronary Intervention as a Predictor of the Transmural Extent of Infarction in Patients With ST-Segment Elevation Anterior Acute Myocardial Infarction", JACC: Cardiovascular Imaging, vol. 2, No. 3, 2009, 10 pages.

Kolli, K. K., et al., "Effect of Varying Hemodynamic and Vascular Conditions on Fractional Flow Reserve: An In Vitro Study", Journal of the American Heart Association, vol. 5, No. 7, Jun. 30, 2016, 13 pages.

Kolossvary et al. 2021 Journal of Cardiovascular Computed Tomography 15: 137a145 (Year: 2020).

Li et al. 2021 Communications Biology 4: article No. 99, 12 pages (Year: 2021).

Lindenauer et al. 2005 N. Engl. J. Med. 353:349-61 (Year: 2005).

Liu et al. 2019 Quant. Imaging Med. Surg. 9:711-721 (Year: 2019).

Oxford English Dictionary, Definition of "pathway" (Year: 1989).

Puelacher et al. 2020 JACC 76:1910-1912 (Year:2020).

Rohrich et al. 2020 Radiology—Cardiothoracic Imaging 2 e190190 (Year: 2020).

Shafiq-ul-Hassan et al. 2017 Med. Phys. 44: 1050-1062 (Year: 2017).

Wilson, R. F., et al., "The effect of coronary angioplasty on coronary flow reserve.", Circulation, vol. 77, No. 4, Apr. 1, 1988, 13 pages.

Yang et al. 2021 JACC Cardiovascular Imaging 14:629-641 (Year: 2021).

Zreik, M., et al., "Deep learning analysis of the myocardium for identification of patients with functionally significant coronary artery stenosis with coronary CT angiography.", Medical Image Analysis, vol. 44, Nov. 16, 2017, 42 pages.

\* cited by examiner

<u>600</u>
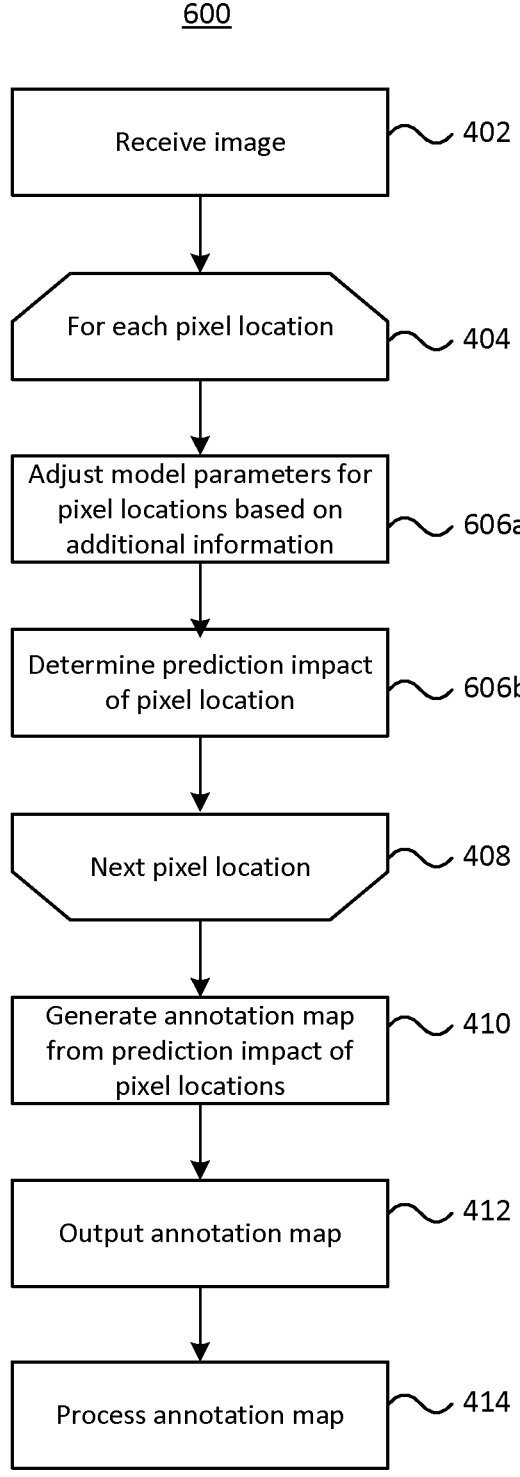
FIG.    6

700
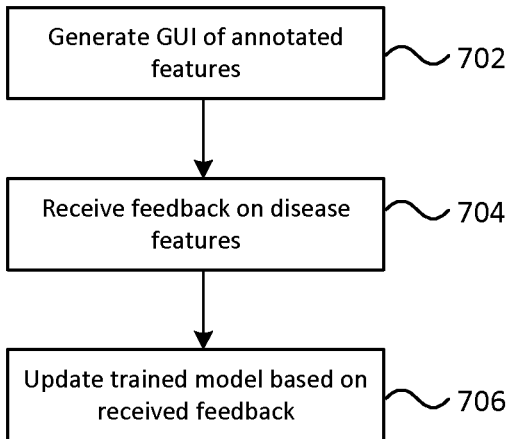
FIG.    7

800
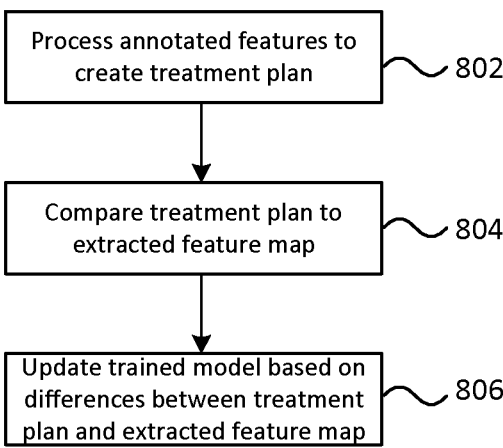
FIG.    8

AUTOMATIC ANNOTATION OF CONDITION FEATURES IN MEDICAL IMAGES

RELATED APPLICATIONS

The current application claims priority to Canadian Patent Application 3,103,872 filed Dec. 23, 2020 and titled "AUTOMATIC ANNOTATION OF CONDITION FEATURES IN MEDICAL IMAGES," the entire contents of which are incorporated herein by reference in their entirety.

TECHNICAL FIELD

The current disclosure relates to processing of medical images and in particular to automatic annotations of features of a condition present in medical images.

BACKGROUND

Medical images are often used to identify potential diseases or conditions. The images can be processed by a professional, or by a trained machine learning model. For example, image segmentation models take an image as input and output a line vector or image mask outlining a particular feature that the model was trained to identify, such as feature associated with a disease or condition. While such image segmentation models can provide relatively accurate segmentation or extraction of the disease features, the models require relatively large training data sets with the input image as well as corresponding annotated features. The annotated features of input images needed for training are often performed manually Hand annotation of features in images to create training data sets can be impractical due to the large number of images necessary and/or the difficulty in annotation numerous small features. Without annotated features, the segmentation model cannot be trained to extract features in unknown images.

While a segmentation model can be trained to extract features in images, a classification model may be trained to classify unknown images into one or more classifications. FIG. 1 depicts such a classification model. As depicted, an untrained model 102 can be trained with a plurality of images that have been labeled as either healthy 104*a*, or disease 104*b*. Similar to the training of the segmentation model, the images may be labelled as either representing a healthy condition, or a disease condition. However, given that images are labelled as being either healthy or having a particular disease or condition present, generating a training dataset may be significantly easier. Once the model 102 has been sufficiently trained, the trained model 106 can be used to classify unknown images 108. The trained model 106 can classify the unknown images as either being healthy 110*a* or representative of a particular disease 110*b*. The trained model 106 may be trained to classifying one or more diseases or conditions.

While classifying models and segmentation models may be useful, it is desirable to have an additional, alternative, and/or improved technique of processing medical images and in particular processing medical images to automatically annotate the medical images.

SUMMARY

In accordance with the current disclosure there is provided a method of annotating medical images comprising: passing a medical image to a trained machine learning (ML)

classification model; receiving from the trained ML classification model classification output comprising a confidence value that a particular condition is present in the medical image; if the confidence in the indicated condition is above a predefined high confidence threshold, processing the medical image to automatically identify key features of the particular condition present in the medical image by: for each of a plurality of pixel groups determining a prediction impact of changes to the respective pixel group has on the trained ML classification output; and outputting an annotation map providing an indication of the key features of the particular condition based on the prediction impact of the plurality of pixel groups.

In accordance with a further embodiment of the method, the predefined confidence threshold is at least 95%.

In accordance with a further embodiment of the method, the predefined confidence threshold is at least 99%.

In accordance with a further embodiment of the method, the GUI allows a user to select one or more key features present in the medical image and remove or modify the selected key feature from the annotation map.

In accordance with a further embodiment of the method, removing the selected key feature from the annotation map is used as feedback for adjusting the trained ML classification model.

In accordance with a further embodiment of the method, the GUI comprises functionality for automatically or semi-automatically identifying unrelated features that are not related to the particular condition and using the identified unrelated features as feedback.

In accordance with a further embodiment of the method, the method further comprises: processing the output annotation map to generate a treatment plan for treating the condition.

In accordance with a further embodiment of the method, processing the output annotation map comprises: generating a treatment map based on the annotation map and including one or more treatment locations corresponding in part to one or more of the key features identified in the annotation map.

In accordance with a further embodiment of the method, generating the treatment map comprises: retrieving one or more additional images associated with the medical image; identifying one or more characteristics in the one or more additional images; and determining one or more key features identified in the annotation map that are suitable for treatment based on the identified one or more characteristics in the one or more additional images.

In accordance with a further embodiment of the method, the method further comprises: generating model feedback based on a comparison of the treatment map and the annotation map; and adjusting the trained ML classification model based on the model feedback.

In accordance with a further embodiment of the method, the method further comprises receiving a medical image over a network from a remote computer system; and returning the annotation map to the remote computer system.

In accordance with a further embodiment of the method, the method further comprises determining a fee associated with returning the annotation map.

In accordance with a further embodiment of the method, the method further comprises training a classification model to provide the trained ML classification model.

In accordance with a further embodiment of the method, training the classification model comprises using data augmentation on labelled training images.

In accordance with a further embodiment of the method, determining the prediction impact of changes to the respective pixel group has on the trained ML classification output uses one or more of: occlusion; and saliency.

In accordance with a further embodiment of the method, at least one pixel group of the plurality of pixel groups comprises a single pixel.

In accordance with a further embodiment of the method, at least one pixel group of the plurality of pixel groups comprises a plurality of adjacent pixels.

In accordance with the present disclosure there is further provided a non-transitory computer readable medium storing instructions which when executed by one or more processors of a system configure the system to provide a method annotating medical images comprising: passing a medical image to a trained machine learning (ML) classification model; receiving from the trained ML classification model classification output comprising a confidence value that a particular condition is present in the medical image; if the confidence in the indicated condition is above a predefined high confidence threshold, processing the medical image to automatically identify key features of the particular condition present in the medical image by: for each of a plurality of pixel groups determining a prediction impact of changes to the respective pixel group has on the trained ML classification output; and outputting an annotation map providing an indication of the key features of the particular condition based on the prediction impact of the plurality of pixel groups.

In accordance with a further embodiment of the non-transitory computer readable medium, the predefined confidence threshold is at least 95%.

In accordance with a further embodiment of the non-transitory computer readable medium, the predefined confidence threshold is at least 99%.

In accordance with a further embodiment of the non-transitory computer readable medium, outputting the annotation map comprises: generating a graphical user interface (GUI) comprising a representation of the annotation map; and outputting the GUI for display on a display device.

In accordance with a further embodiment of the non-transitory computer readable medium, the GUI allows a user to select one or more key features present in the medical image and remove or modify the selected key feature from the annotation map.

In accordance with a further embodiment of the non-transitory computer readable medium, removing the selected key feature from the annotation map is used as feedback for adjusting the trained ML classification model.

In accordance with a further embodiment of the non-transitory computer readable medium, the GUI comprises functionality for automatically or semi-automatically identifying unrelated features that are not related to the particular condition and using the identified unrelated features as feedback.

In accordance with a further embodiment of the non-transitory computer readable medium, the method provided by execution of the instructions further comprises: processing the output annotation map to generate a treatment plan for treating the condition.

In accordance with a further embodiment of the non-transitory computer readable medium, processing the output annotation map comprises: generating a treatment map based on the annotation map and including one or more treatment locations corresponding in part to one or more of the key features identified in the annotation map.

In accordance with a further embodiment of the non-transitory computer readable medium, generating the treatment map comprises: retrieving one or more additional images associated with the medical image; identifying one or more characteristics in the one or more additional images; and determining one or more key features identified in the annotation map that are suitable for treatment based on the identified one or more characteristics in the one or more additional images.

In accordance with a further embodiment of the non-transitory computer readable medium, the method provided by execution of the instructions further comprises: generating model feedback based on a comparison of the treatment map and the annotation map; and adjusting the trained ML classification model based on the model feedback.

In accordance with a further embodiment of the non-transitory computer readable medium, the method provided by execution of the instructions further comprises: receiving a medical image over a network from a remote computer system; and returning the annotation map to the remote computer system.

In accordance with a further embodiment of the non-transitory computer readable medium, the method provided by execution of the instructions further comprises determining a fee associated with returning the annotation map.

In accordance with a further embodiment of the non-transitory computer readable medium, the method provided by execution of the instructions further comprises training a classification model to provide the trained ML classification model.

In accordance with a further embodiment of the non-transitory computer readable medium, training the classification model comprises using data augmentation on labelled training images.

In accordance with a further embodiment of the non-transitory computer readable medium, determining the prediction impact of changes to the respective pixel group has on the trained ML classification output uses one or more of: occlusion; and saliency.

In accordance with a further embodiment of the non-transitory computer readable medium, at least one pixel group of the plurality of pixel groups comprises a single pixel.

In accordance with a further embodiment of the non-transitory computer readable medium, at least one pixel group of the plurality of pixel groups comprises a plurality of adjacent pixels.

In accordance with the present disclosure there is further provided a system for annotating medical images comprising: at least one processor; at least one memory storing instructions, which when executed by the at least one processor configure the system to provide a method of annotating medical images comprising: passing a medical image to a trained machine learning (ML) classification model; receiving from the trained ML classification model classification output comprising a confidence value that a particular condition is present in the medical image; if the confidence in the indicated condition is above a predefined high confidence threshold, processing the medical image to automatically identify key features of the particular condition present in the medical image by: for each of a plurality of pixel groups determining a prediction impact of changes to the respective pixel group has on the trained ML classification output; and outputting an annotation map providing an indication of the key features of the particular condition based on the prediction impact of the plurality of pixel groups.

In accordance with a further embodiment of the system, the predefined confidence threshold is at least 95%.

In accordance with a further embodiment of the system, the predefined confidence threshold is at least 99%.

In accordance with a further embodiment of the system, outputting the annotation map comprises: generating a graphical user interface (GUI) comprising a representation of the annotation map; and outputting the GUI for display on a display device.

In accordance with a further embodiment of the system, the GUI allows a user to select one or more key features present in the medical image and remove or modify the selected key feature from the annotation map.

In accordance with a further embodiment of the system, removing the selected key feature from the annotation map is used as feedback for adjusting the trained ML classification model.

In accordance with a further embodiment of the system, the GUI comprises functionality for automatically or semi-automatically identifying unrelated features that are not related to the particular condition and using the identified unrelated features as feedback.

In accordance with a further embodiment of the system, the method provided by execution of the instructions further comprises: processing the output annotation map to generate a treatment plan for treating the condition.

In accordance with a further embodiment of the system, processing the output annotation map comprises: generating a treatment map based on the annotation map and including one or more treatment locations corresponding in part to one or more of the key features identified in the annotation map.

In accordance with a further embodiment of the system, generating the treatment map comprises: retrieving one or more additional images associated with the medical image; identifying one or more characteristics in the one or more additional images; and determining one or more key features identified in the annotation map that are suitable for treatment based on the identified one or more characteristics in the one or more additional images.

In accordance with a further embodiment of the system, the method provided by execution of the instructions further comprises: generating model feedback based on a comparison of the treatment map and the annotation map; and adjusting the trained ML classification model based on the model feedback.

In accordance with a further embodiment of the system, the method provided by execution of the instructions further comprises: receiving a medical image over a network from a remote computer system; and returning the annotation map to the remote computer system.

In accordance with a further embodiment of the system, the method provided by execution of the instructions further comprises determining a fee associated with returning the annotation map.

In accordance with a further embodiment of the system, the method provided by execution of the instructions further comprises training a classification model to provide the trained ML classification model.

In accordance with a further embodiment of the system, training the classification model comprises using data augmentation on labelled training images.

In accordance with a further embodiment of the system, determining the prediction impact of changes to the respective pixel group has on the trained ML classification output uses one or more of: occlusion; and saliency.

In accordance with a further embodiment of the system, at least one pixel group of the plurality of pixel groups comprises a single pixel.

In accordance with a further embodiment of the system, at least one pixel group of the plurality of pixel groups comprises a plurality of adjacent pixels.

BRIEF DESCRIPTION OF THE DRAWINGS

Further features and advantages of the present disclosure will become apparent from the following detailed description, taken in combination with the appended drawings, in which:

FIG. 5 depicts a system for automatically annotating disease features, planning a treatment of the disease and carrying out the treatment plan;

FIG. 6 depicts a method of automatically annotating a medical image;

FIG. 7 depicts a method of updating a trained model; and

FIG. 8 depicts a further method of updating a trained model.

DETAILED DESCRIPTION

Figure 1:
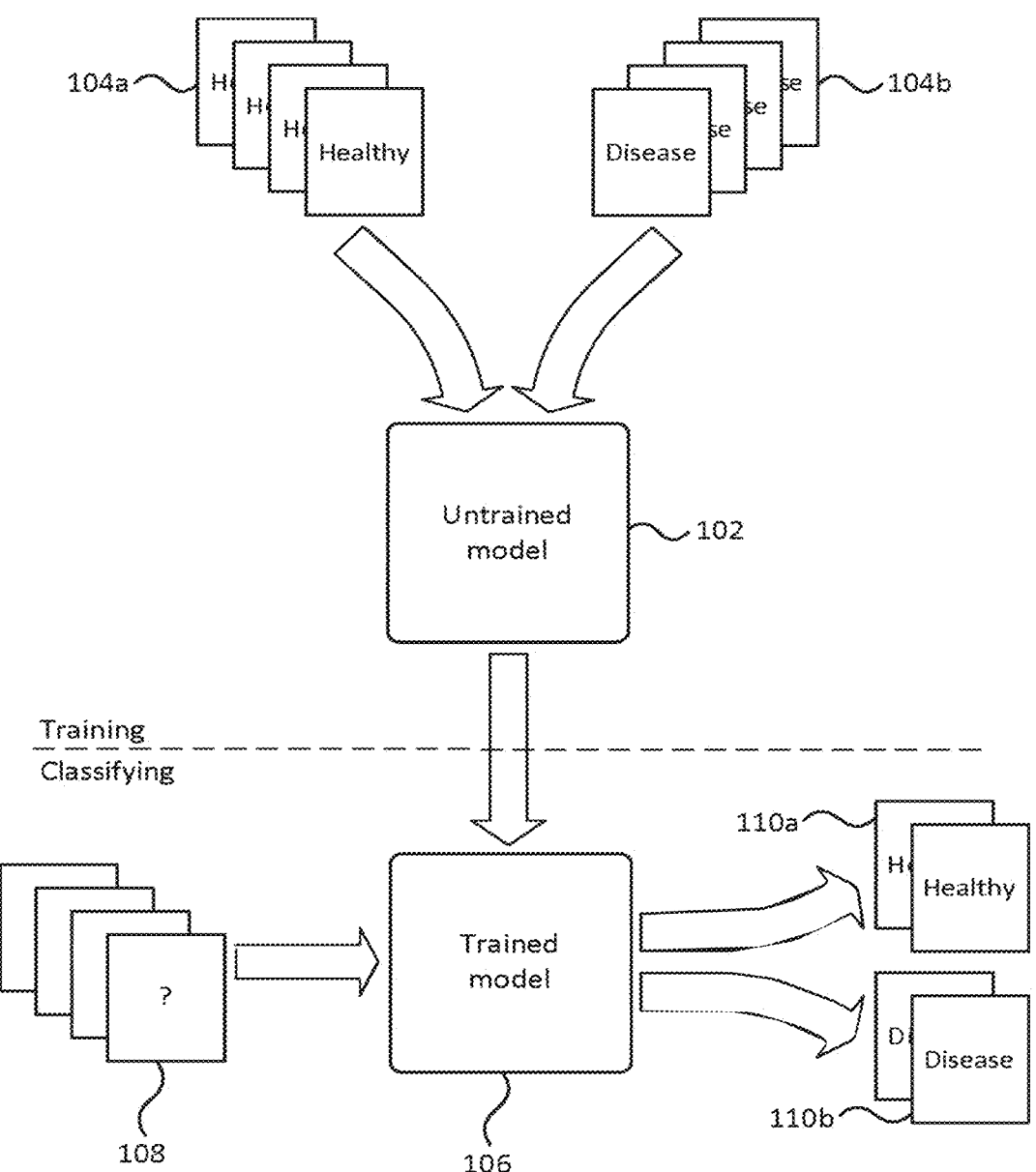
FIG. 1 depicts training and using a machine learning classification model.

An automatic annotation system is described further below that can automatically extract and annotate features in a medical image. The automatic extraction allows features, which can include features indicative of a particular disease, to be extracted from the images. As described further below, rather than using a trained segmentation model to extract the features, the process uses a trained classification model in conjunction with input modification to identify the locations within the input images that cause the image to be classified as healthy vs diseased. The automatic feature annotation may not perform acceptably well if the classification model cannot classify the image with a high degree of confidence. As such, the process first classifies images as healthy or diseased, and then if the disease prediction confidence is above a threshold, such as 95%, the features can be automatically extracted using input modification. The identified features may be further processed for example to automatically annotate individual features, which may in turn be used for various applications. For example, the annotated features may be used in planning a treatment of the disease. In cases where an abundance of input images are available with appropriate labels, such as "Healthy image", "Disease A image", "Disease B image", it is possible to use these labels to train a classification network that can then be used to provide the annotation/feature extraction output.

The first step in training the automatic feature extraction is to train a classification model for one or more of the labels. The model can have any structure, but since a very high accuracy is required, models may be chosen based on the best performing image classification models such as xception, resnext, or mnastnet. As an example, a model in accordance with the current disclosure that provides retina classification may be xception with additional layers added for image downscaling. The retina classification model was trained to 99.9% accuracy from 3,000 images with 2 class labels of "Healthy" and "Diabetic Retinopathy". In order to increase the training data available, training data augmentation may be used, which adjusts or modifies training images for example by rotating, stretching, mirroring, or adjusting other characteristics to generate additional images. Data augmentation may help avoid or reduce overfitting the classification model to available images.

After training the classification model, the trained model can be applied to unknown images in order to classify them as healthy or indicative of diabetic retinopathy. If the prediction confidence of the diabetic retinopathy is above a prediction threshold, the unknown input image is used with input modification to determine portions of the image that impact the classification result of the classification model. The input modification may use one of several algorithms to modify the input image when extracting the features from the images. For example, occlusion involves evaluating the input image using the classification model multiple times with a square mask hiding some pixels in the input image in each classification attempt. Each time the model is evaluated, the mask is translated across the image and the value of the output class of interest is recorded. A 2D map may then be plotted of the output class value corresponding to the mask position (x,y). The resulting 2D map reveals the features of interest.

Occlusion can be very inefficient and inaccurate compared to other methods. For example, saliency is another technique which calculates the gradients of the input image for the classification model. The gradient indicates the change in the output for changes to the input. Where the occlusion process actually changes the input and determines the output of the model, the saliency process mathematically determines the changes in the output based on input changes by determining the input gradient, or image gradient, of the classification model. The input gradient may be defined as:

$$\text{Input Gradient }(x, y) = \frac{\partial c_i}{\partial a_{x,y}}$$

Where:

$c_i$ is the model output for the desired class for feature extraction i $a_{x,y}$ is the model input or input image pixel at location (x,y)

The gradient may calculated mathematically and be used directly for features extraction to identify the locations in the input image that have the largest impact on the classification. Other techniques that may be used for the input modification may include guided backpropagation, integrative gradients, noise tunneling gradient, etc.

Figure 2:
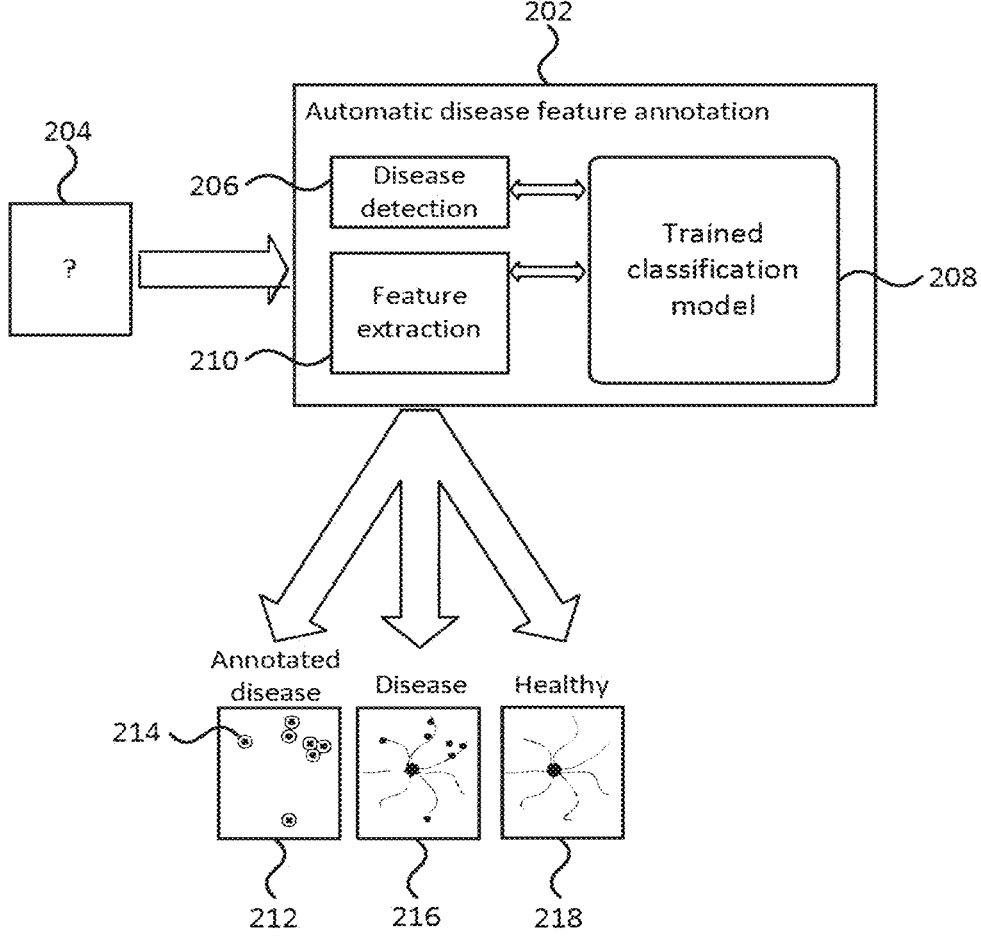
FIG. 2 depicts automatic disease feature annotation functionality.

FIG. 2 depicts automatic disease feature annotation functionality. Although not depicted in FIG. 2, the automatic disease feature annotation functionality 202 may be implemented by one or more computer systems comprising one or more processors executing instructions stored in one or more memory units that configure the computer systems to implement the functionality. The automatic disease feature annotation functionality 202 can process one or more input images 204. The input image 204 is a medical image such as an image of the eye, or part of the eye; however, other medical images may be used including for example, ultrasound images, MRI images, x-ray images, light microscopy, 2-photon microscopy, confocal microscopy, optical coherence tomography, photoacoustic imaging, histological slide, etc. The image 204 may be processed by disease detection functionality 206 that determines the presence or absence of a particular disease a trained classification model 208 is trained to identify. The trained classification model 208 may be trained to classify one or more diseases or conditions. Additionally, although only a single trained classification model is depicted in FIG. 2, it is possible for the disease detection functionality 206 to pass the input image 204 to a plurality of different trained classification models that are trained to detect different diseases/conditions.

The trained classification model 208 receives the input image and provides a classification output indicative of one or more labels that the model is trained to identify. The classification model may be provided by, or based on, various network architectures including for example, xception, resnext, or mnastnet. The output from the trained model includes an indication of the prediction confidence. If the prediction confidence is above a first high threshold, such as 95% or higher, for a particular disease label the image 204 may then be processed by feature extraction functionality 210. The feature extraction functionality uses input modification techniques, such as occlusion, saliency, guided backpropagation, integrative gradients, noise tunneling gradient, etc., to determine the importance of pixels in the input image in arriving at the classification. The feature extraction functionality generates a feature extraction map indicating the impact of changing particular pixel values has on the classification output. The feature extraction map may be used to automatically annotate the disease features present in the image. As depicted, the automatic disease feature annotation functionality 202 may categorize the image as having a particular disease or condition present 212 as well as highlighting the extracted features as depicted schematically by circles 214. If the prediction confidence is below the high threshold, but above a low threshold for the disease or condition, the automatic disease feature annotation functionality 202 can identify a disease present in the image, but not with a high enough accuracy in order to automatically extract the disease features. In such cases, the automatic disease annotation functionality 202 classifies the image as having the disease 216 but does not annotate any features. The automatic disease annotation functionality 202 can also classify the image as healthy 218 if the output from the trained classification model indicates that it is a healthy image.

The features highlighted by the automatic feature extraction may be used directly as the annotated disease features. Alternatively, the highlighted features may be further processed in order to generate the annotated disease features. The extracted features may highlight features present in the image that are not in fact part of the disease. For example, in images of the eye, the feature extraction may highlight parts of the eye such as the macula, optic nerve, blood vessels etc. along with disease features such as microaneurysms associated with the disease/condition diabetic retinopathy. The extracted features may be processed to remove the non-disease features to provide the annotated disease features. If the annotated disease features differ from the extracted features, the annotated disease features, or the difference(s) between the extracted features and annotated disease features, may be used as feedback for further training or updating of the trained classification model.

Figure 3:
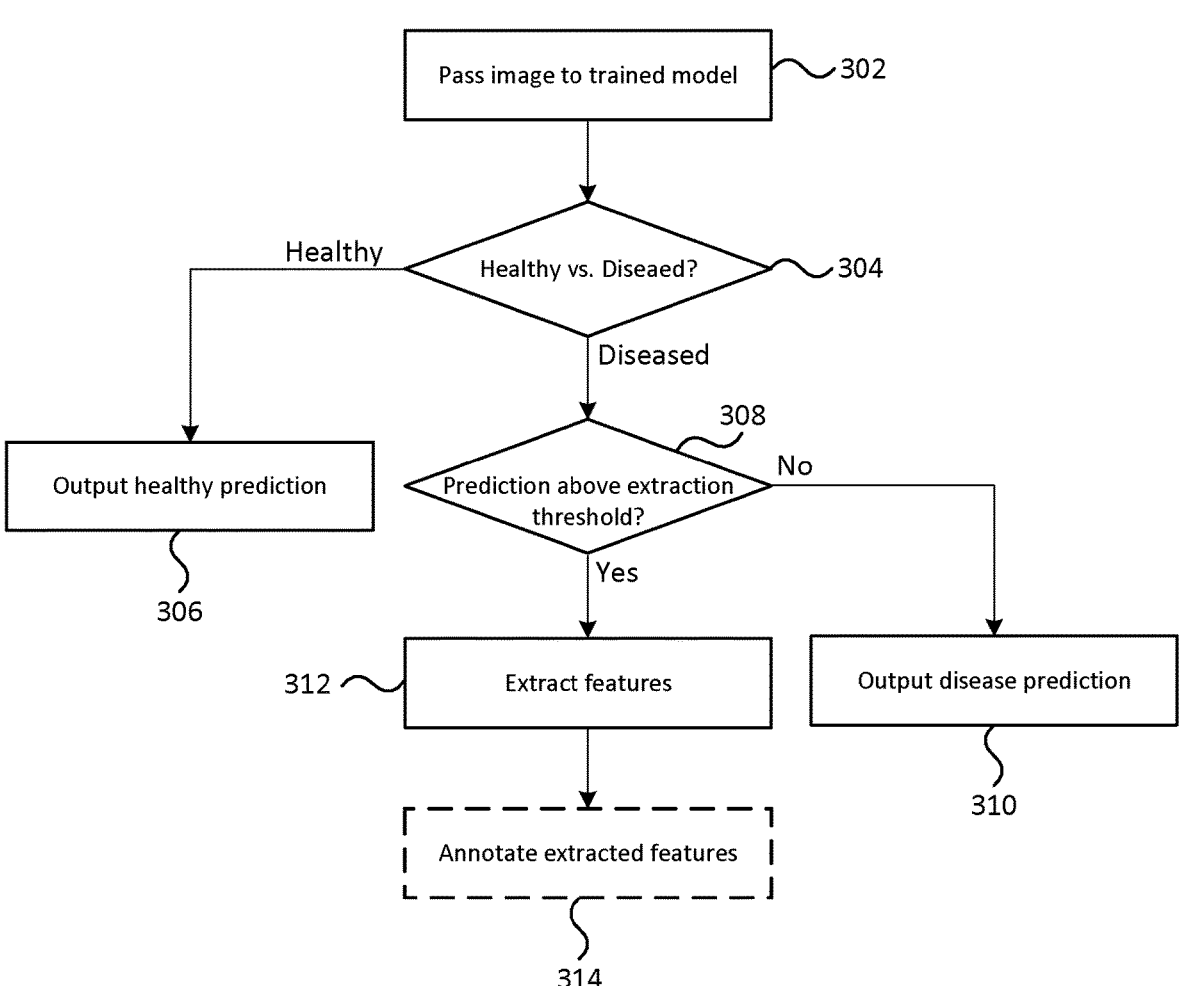
FIG. 3 depicts a method of automatically annotating disease features in medical images.

FIG. 3 depicts a method of automatically classifying medical images and extracting features. The method 300 may be performed by a computer system that may receive medical images. The computer system implementing the method 300 may be connected directly to, or be part of the, the imaging system capturing the medical images or may be separate from such imaging systems. Regardless of the particular location or integration of the computer system, the method 300 passes an image to a trained classification model (302). The classification model is trained to classify an image as either being healthy or indicative of a particular disease the model has been trained to recognize. The model may be trained to recognize one or more diseases or conditions. In addition to providing an indication of the disease classification, the model also provides an indication of the confidence that the model's classification is correct. Once the output is received from the classification model it is determined whether the image was classified as healthy or diseased (304). If the image is classified as healthy (Healthy at 304), the method outputs the healthy prediction (306). The model may explicitly classify the image as being healthy. Additionally or alternatively, disease classifications that are below some prediction confidence threshold may be considered as being healthy.

When the image is classified as a diseased or not healthy (Diseased at 304), the method 300 determines if the prediction confidence is above a feature extraction threshold (308). In order to properly extract features, it is necessary that the classification of the input image be above a certain confidence level, which may be for example 95% or higher. The confidence level in the classification prediction necessary in order to extract features may be referred to as an extraction threshold. If the prediction confidence is below the extraction threshold (No at 308) the disease prediction from the classification model is output (310). If however, the prediction confidence is above the extraction threshold (Yes at 308), the method proceeds to extract the features from the image (312). The feature extraction relies upon the classification model in order to identify the features, or portions of the image, the result in the classification and as such in order to provide acceptable feature extraction results, the classification provided by the model must be sufficiently accurate, i.e. have high confidence in the prediction. The extracted features may be provided as a single 2D map or as a plurality of 2D maps. For example, respective 2D feature maps may be generated for red, green, blue (RGB) channels of an image, or other channels depending upon the channels used in the input image. Further, one or more individual 2D maps may be combined together into a 2D map.

Once the features are extracted, the features can be further processed, for example to further annotate the extracted features (314). Where the extracted features may be provided as a 2D map or mask providing locations within the input image that result in the disease classification, annotating the extracted features may result in individual objects each representing a particular feature or group of features. For example, for diabetic retinopathy, and individual annotated feature may be the location within the input image of a micro-aneurism.

Figure 4:
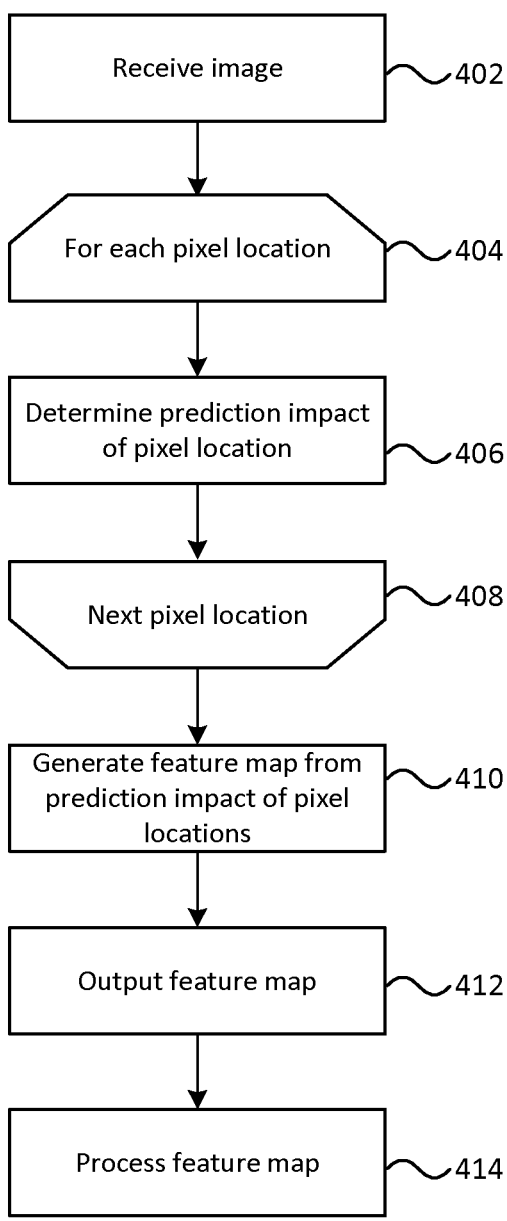
FIG. 4 depicts a further method of automatically annotating disease features in medical images.

FIG. 4 depicts a method of automatically extracting disease features in medical images. The method 400 assumes that the image has been classified as being indicative of a disease by a trained classification model and that the classification confidence is above a threshold for performing feature extraction using the classification model. The method 400 receives the image (402) and then for each pixel location (404, 408) in the image, the method determines the prediction impact of the pixel location (406) until all of the pixel locations have been determined. Each of the pixel locations may be individual pixels or groups of pixels. Determining the impact of the pixel location on the prediction may be done in various ways such as by occlusion in which the pixel value(s) of the location are changed, for example to all black, white, grey or other color, and then the adjusted image provided to the trained classification model in order to classify the adjusted image which can then be compared to the baseline prediction from the original input image. Other techniques for determining the impact that different pixel locations have on the classification output from the classification model may be used, including for example saliency, which determines the input/image gradient of the model which in turn provides the impact changing the input has on the output, or the impact changing values at pixel locations has on the classification. The impact of the different pixel locations may be determined individually, one at a time or in parallel, or the different pixel locations can be calculated all at once for example by determining the gradient of the classification model.

After the prediction impact of all of the pixel locations is determined, a feature extraction map can be generated (410) based on the impact of the pixel locations. The feature extraction map may be a 2D map or image indicative of the impact the different pixel locations have on the classification. The 2D feature map may be output (412) to other processes or functionality, for example for display or further processing (414). The feature map may be further processed in order to identify and annotate individual features. For example, the feature map may highlight individual features such as blood vessels, optical nerve, micro-aneurysms, drusen, etc. Each feature may be annotated. The individual feature annotation may be done automatically by processing the locations of the input image that are highlighted by the feature map. Each individual annotated feature may provide annotated feature information such as an identifier or name for the individual feature, annotated feature details, such as the location within the image, the shape of the feature, etc. The annotated features, or the 2D map of extracted features may be used for various purposes including for example, in planning a treatment of the disease condition.

Figure 5:
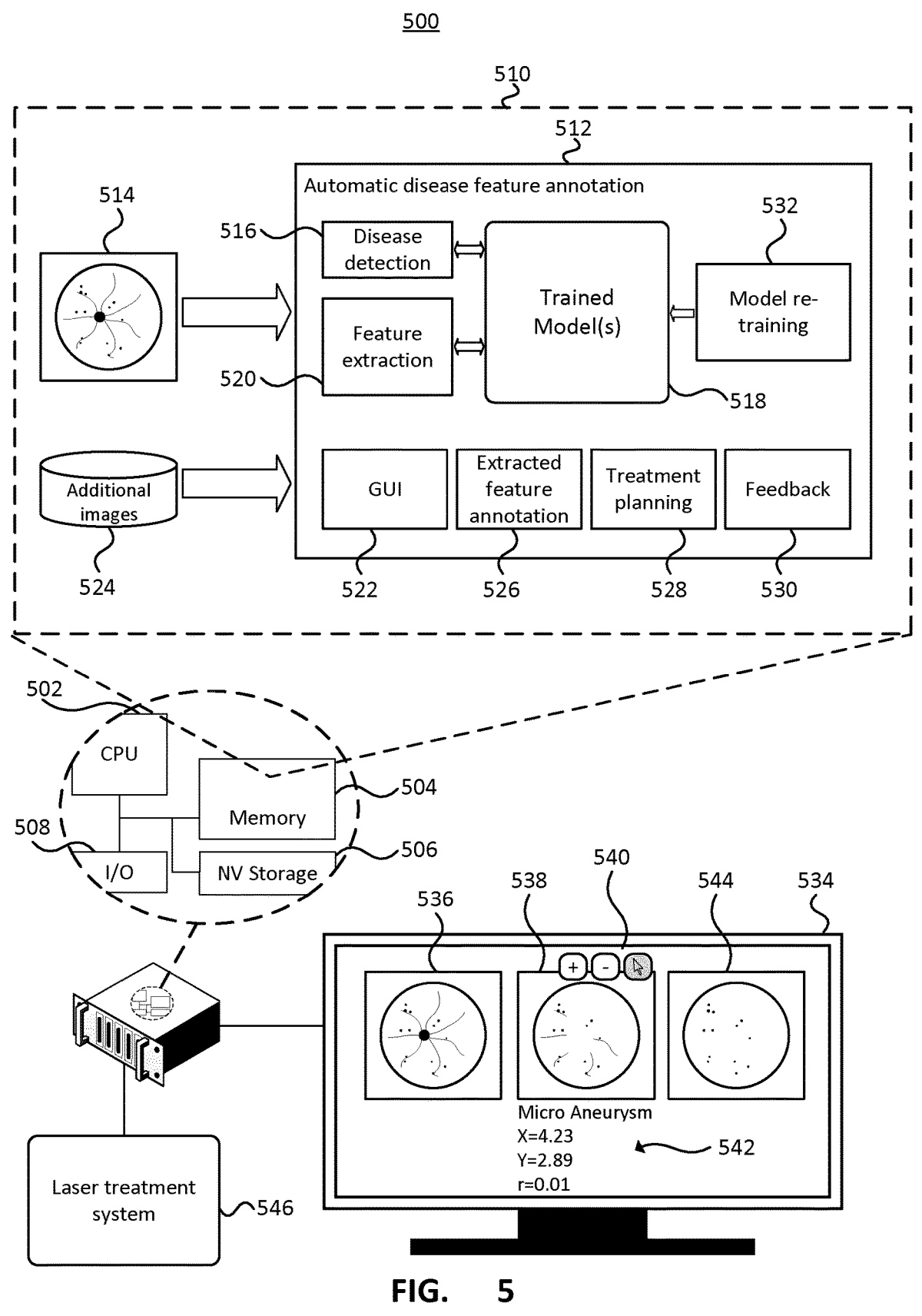

FIG. 5 depicts a system for automatically annotating disease features, planning a treatment of the disease and carrying out the treatment plan. The system 500 is depicted as comprising a server that implements various functionality. Although depicted as a single server, the functionality or portions of the functionality maybe implemented by a plurality of servers or computing systems The server comprises a CPU 502 for executing instructions, a memory 504 for storing instructions, a non-volatile (NV) storage element 506 and an input/output (IO) interface 508 for connecting input and/or output devices to the server. The instructions and data stored in the memory 504, when executed by the CPU 502 configure the server to provide various functionality 510.

The functionality 510 includes automatic disease feature annotation functionality 512. The annotation functionality 512 may receive medical images 514, depicted as a fundus image of an eye although the functionality may be applied to other types of medical images. Disease detection functionality 516 may receive the image and pass it to one or more trained classification models 518 that are trained to classify images as healthy or diseased. The trained model 518 also provides an indication of the prediction confidence of the classification of the trained model 518. If the prediction confidence is above a feature extraction threshold, which may be for example 95% or higher, feature extraction functionality 520 can further process the image to extract features. As described above, the feature extraction may use the trained classification model as well as input modification in order to identify the features in the image.

The extracted features, which may be provided as a 2D map highlighting locations within the image that impact the classification results, can be further processed. For example, graphical user interface (GUI) functionality 522 can process the extracted features to generate a GUI that displays the extracted features, or a representation of the extracted features. The GUI provided by the GUI functionality 522 may also provide additional functionality, for example it may provide the ability to interact with the features including possibly manually adding, removing, or adjusting the features, as well as displaying other information such as patient details, original images, other medical images 524, etc.

The extracted features may also be processed by extracted feature annotation functionality 526. While the extracted features highlighted by the feature extraction functionality 520 provide indications of important features the trained model used to classify the image as diseased, the extracted features may include features that are not disease features but rather common features to the organ being imaged, such as the eye. These common features may be identified using trained models that have been trained to identify the common features, for example using images with and without the common feature present. Further, the extracted features are provided as a 2D image map which highlights the locations of the features in the image, however it does not provide individual features. The extracted feature annotation functionality 526 may identify individual features from the extracted features and generate corresponding individual annotated features. The extracted feature annotation functionality 526 may process the extracted feature map to identify the individual features using various techniques including for example image processing techniques that can process the 2D feature map, and possibly the input image, to separate individual features. Once the individual features are identified, corresponding individual annotated features can be generated including information about the annotated feature such as the location within the image, the size and or shape of the annotated feature, an identifier and/or name, notes or comments about the annotated feature, etc. The extracted feature annotation functionality may generate annotated features corresponding to each of the individual extracted features, or may generate annotated features corresponding to a subset of the extracted features such as only those individual features that are not common to imaged organ. That is, common features such as blood vessels, optic nerves, etc. may not be processed to corresponding annotated features. Additionally or alternatively, the extracted feature annotation functionality may include functionality for manually adding/removing annotated features.

The extracted features, or the annotated features generated from the extracted features may be processed by treatment planning functionality 528. The treatment planning functionality may utilize machine learning techniques to identify portions of the extracted and/or annotated features that can be treated. The treatment planning functionality may utilize additional information, such as additional medical images 524, in planning the treatment. For example, in treating an ocular condition, a fundus image may be processed in order to identify features that may be treated and additional images may identify additional information such as a thickness of the retina that can help select a subset of the features for actual treatment.

Feedback functionality 530 can generate feedback that may be used, for example by model re-training functionality 532, or other models, such as those used in treatment planning or annotating extracted features. The feedback may be generated in various ways. For example, the feedback can be generated directly from manual interactions of a user such as manually removing features or annotated features. The feedback may be generated by comparing a treatment plan, which may provide an indication of the important features for treating the condition of disease, to the extracted features. The feedback may be used to train or adjust the classification model in order to classify the images based on only those features that can be treated.

As depicted, the system 500, may include a display or monitor 534 for displaying a GUI that allows an operator to interact with the system. It will be appreciated that the GUI depicted in FIG. 5 is only illustrative and an actual GUI may present desired information in a wide range of formats. As depicted the GUI may display various information including an input image 536, which is depicted as a fundus image of the eye although other medical images may be used. The GUI may include an image of the individual annotated features 538. The GUI may provide controls 540 that allow the operator to interact with the individual annotated features. For example, the controls may allow the operator to select an individual annotated feature and adjust information 542, such as its location, size, shape, name, notes, etc. Additionally, the controls may include functionality to allow the operator to remove an annotated feature, or possibly add or define new annotated features. The functionality for modifying annotated features may provide functionality to allow an operator to manually add, remove or modify annotated features. Additionally or alternatively, the functionality for modifying annotated features may perform the modifications automatically or semi-automatically for example requiring some user input to define a general region of a possible annotated feature to be modified and/or confirming or rejecting possible modifications. The GUI may also display a treatment plan 544 for treating the condition. Although not depicted in FIG. 5, the GUI may provide controls to the operator for adjusting the treatment plan. The GUI may provide indications of any of the changes made by the operator to the feedback functionality in order to possibly adjust how features are identified and/or annotated.

The system 500 may also be coupled to a treatment system 546, which is depicted as being a laser treatment system, although other treatment systems may be used. The treatment system may carry out the treatment plan for example by treating the determined location with the laser.

The above has depicted the various functionality being provided by a single server that may be directly connected to a treatment system 546. The functionality may be provided by one or more networked systems. For example the disease detection functionality 516, trained models 518, and feature extraction functionality 520 may be implemented in one or more cloud servers that can be accessed by different professionals, possibly for a fee. The cloud based functionality may interact with other computer systems or controllers such as controllers of treatment systems. Further still, the results of the feature extraction may be used to identify features to be treated or the output may be provided as input to other systems, for example for training other models, etc.

FIG. 6 depicts a method of automatically extracting disease features in medical images. The method 600 is similar to the method 400, with similar steps using similar reference numbers which will not be described again in detail. As described above, in annotating features and planning treatment, the functionality may make use of additional medical images. The method 600 utilizes additional images when extracting the features. The additional images or information are used when processing each of the pixel locations (404, 408). The additional images or information may be used to adjust model parameters for the pixel locations (606*a*) and then the prediction impact of the pixel location determined using the adjusted parameters (606*b*). The additional information may be used to locally tune the classification model. For example, the model could be tuned to be more sensitive in pixel locations in which there are a number of other features and less sensitive in other areas. The additional information may include additional medical images, patient information, information from other pixel locations, etc.

FIG. 7 depicts a method of updating a trained model. The method 700 generates and displays a GUI of the annotated feature (702). The GUI may allow a user to interact with the annotated features, including for example selecting one or more of the annotated features and deleting or changing the selected feature, or selecting a location in the image and creating a new annotated feature. Regardless of the interaction that adjusts the annotated features, the feedback from the GUI of the updated annotated features are received as feedback on the disease features (704). The trained classification model, and/or models used for automatically generating annotated features from extracted features, may be updated or re-trained based on the received feedback (706).

FIG. 8 depicts a further method of updating a trained model. The method 800 processes annotated features in order to create a treatment plan (802) for treating the disease present in the medical image. The treatment plan may specify locations for treating with a system such as a laser or ultrasound device. The treatment plan may provide a good indication of relevant features of the disease. The treatment plan is compared to the extracted feature map (804) and the trained classification model, and/or models used for automatically generating annotated features from extracted features, is updated or re-trained based on the differences between the treatment plan and the extracted feature map (806).

The above has described the use of feedback to re-train models. In addition to using feedback from the GUI or differences between extracted features and a treatment plan as described above, other information may be used to identify extracted features that may not be important in the identification of a disease or its treatment. For example, in detection or treatment of an eye disease, extracted features may include not only disease features but also features of the eye such as veins or other structures. These common structures may be identified using other techniques, such as other machine learning models trained to identify only those features or structures identified from images. These identified structures may then be removed from the extracted disease features. The modification process may be an iterative process or a trial and error process that repeatedly attempts to identify different features or changes to features until a certain outcome is reached. The modified extracted features with common features removed may then be used to retrain the classification model in order to focus the model on the disease features. Additionally, the above has described using classification model to identify certain disease features and then using feedback to improve the training of the classification model to better identify the disease features. The disease features identified using a particular classification model may also be used to identify features that should be ignored by another classification model. For example, microaneurysm may be important for identifying and/or treating diabetic retinopathy, however are unimportant, and should be ignored, for other conditions or diseases.

It will be appreciated by one of ordinary skill in the art that the system and components shown in FIGS. 1-4 may include components not shown in the drawings. For simplicity and clarity of the illustration, elements in the figures are not necessarily to scale, are only schematic and are non-limiting of the elements structures. It will be apparent to persons skilled in the art that a number of variations and modifications can be made without departing from the scope of the invention as defined in the claims.

Although certain components and steps have been described, it is contemplated that individually described components, as well as steps, may be combined together into fewer components or steps or the steps may be performed sequentially, non-sequentially or concurrently. Further, although described above as occurring in a particular order, one of ordinary skill in the art having regard to the current teachings will appreciate that the particular order of certain steps relative to other steps may be changed. Similarly, individual components or steps may be provided by a plurality of components or steps. One of ordinary skill in the art having regard to the current teachings will appreciate that the components and processes described herein may be provided by various combinations of software, firmware and/or hardware, other than the specific implementations described herein as illustrative examples.

The techniques of various embodiments may be implemented using software, hardware and/or a combination of software and hardware. Various embodiments are directed to apparatus, e.g. a node which may be used in a communications system or data storage system. Various embodiments are also directed to non-transitory machine, e.g., computer, readable medium, e.g., ROM, RAM, CDs, hard discs, etc., which include machine readable instructions for controlling a machine, e.g., processor to implement one, more or all of the steps of the described method or methods.

Some embodiments are directed to a computer program product comprising a computer-readable medium comprising code for causing a computer, or multiple computers, to implement various functions, steps, acts and/or operations, e.g. one or more or all of the steps described above. Depending on the embodiment, the computer program product can, and sometimes does, include different code for each step to be performed. Thus, the computer program product may, and sometimes does, include code for each individual step of a method, e.g., a method of operating a communications device, e.g., a wireless terminal or node. The code may be in the form of machine, e.g., computer, executable instructions stored on a computer-readable medium such as a RAM (Random Access Memory), ROM (Read Only Memory) or other type of storage device. In addition to being directed to a computer program product, some embodiments are directed to a processor configured to implement one or more of the various functions, steps, acts and/or operations of one or more methods described above. Accordingly, some embodiments are directed to a processor, e.g., CPU, configured to implement some or all of the steps of the method(s) described herein. The processor may be for use in, e.g., a communications device or other device described in the present application.

Numerous additional variations on the methods and apparatus of the various embodiments described above will be apparent to those skilled in the art in view of the above description. Such variations are to be considered within the scope.

What is claimed is:

1. A method of annotating medical images comprising:
   passing a medical image to a trained machine learning (ML) classification model;
   receiving from the trained ML classification model classification output comprising a confidence value that a particular condition is present in the medical image;
   if the confidence in the indicated condition is above a predefined high confidence threshold, processing the medical image to automatically identify key features of the particular condition present in the medical image by:

for each of a plurality of pixel groups determining a prediction impact of changes to the respective pixel group has on the trained ML classification output; and outputting an annotation map providing an indication of the key features of the particular condition based on the prediction impact of the plurality of pixel groups, wherein outputting the annotation map comprises:

generating a graphical user interface (GUI) comprising a representation of the annotation map; and outputting the GUI for display on a display device, wherein the GUI comprises functionality for automatically or semi-automatically identifying unrelated features that are not related to the particular condition and using the identified unrelated features as feedback.

2. The method of claim 1, wherein the predefined high confidence threshold is at least 95%.

3. The method of claim 1, wherein the predefined high confidence threshold is at least 99%.

4. The method of claim 1, wherein the GUI allows a user to select one or more key features present in the medical image and remove or modify the selected key feature from the annotation map.

5. The method of claim 4, wherein removing the selected key feature from the annotation map is used as feedback for adjusting the trained ML classification model.

6. The method of claim 1, further comprising:

processing the output annotation map to generate a treatment plan for treating the condition.

7. The method of claim 6, wherein processing the output annotation map comprises:

generating a treatment map based on the annotation map and including one or more treatment locations corresponding in part to one or more of the key features identified in the annotation map.

8. The method of claim 7, wherein generating the treatment map comprises:

retrieving one or more additional images associated with the medical image;

identifying one or more characteristics in the one or more additional images; and determining one or more key features identified in the annotation map that are suitable for treatment based on the identified one or more characteristics in the one or more additional images.

9. The method of claim 7, further comprising:

generating model feedback based on a comparison of the treatment map and the annotation map; and adjusting the trained ML classification model based on the model feedback.

10. The method of claim 1, further comprising:

receiving a medical image over a network from a remote computer system; and returning the annotation map to the remote computer system.

11. The method of claim 1, further comprising training a classification model to provide the trained ML classification model.

12. The method of claim 11, wherein training the classification model comprises using data augmentation on labelled training images.

13. The method of claim 1, wherein determining the prediction impact of changes to the respective pixel group has on the trained ML classification output uses one or more of:

occlusion; and saliency.

14. The method of claim 1, wherein at least one pixel group of the plurality of pixel groups comprises a single pixel.

15. The method of claim 1, wherein at least one pixel group of the plurality of pixel groups comprises a plurality of adjacent pixels.

16. A non-transitory computer readable medium storing instructions which when executed by one or more processors of a system configure the system to provide a method annotating medical images comprising:

passing a medical image to a trained machine learning (ML) classification model;

receiving from the trained ML classification model classification output comprising a confidence value that a particular condition is present in the medical image;

if the confidence in the indicated condition is above a predefined high confidence threshold, processing the medical image to automatically identify key features of the particular condition present in the medical image by:

for each of a plurality of pixel groups determining a prediction impact of changes to the respective pixel group has on the trained ML classification output; and outputting an annotation map providing an indication of the key features of the particular condition based on the prediction impact of the plurality of pixel groups, wherein outputting the annotation map comprises:

generating a graphical user interface (GUI) comprising a representation of the annotation map; and outputting the GUI for display on a display device, wherein the GUI comprises functionality for automatically or semi-automatically identifying unrelated features that are not related to the particular condition and using the identified unrelated features as feedback.

17. A system for annotating medical images comprising:

at least one processor;

at least one memory storing instructions, which when executed by the at least one processor configure the system to provide a method of annotating medical images comprising:

passing a medical image to a trained machine learning (ML) classification model;

receiving from the trained ML classification model classification output comprising a confidence value that a particular condition is present in the medical image;

if the confidence in the indicated condition is above a predefined high confidence threshold, processing the medical image to automatically identify key features of the particular condition present in the medical image by:

for each of a plurality of pixel groups determining a prediction impact of changes to the respective pixel group has on the trained ML classification output; and outputting an annotation map providing an indication of the key features of the particular condition based on the prediction impact of the plurality of pixel groups, wherein outputting the annotation map comprises:

generating a graphical user interface (GUI) comprising a representation of the annotation map; and outputting the GUI for display on a display device, wherein the GUI comprises functionality for automatically or semi-automatically identifying unrelated features that are not related to the particular condition and using the identified unrelated features as feedback.

\* \* \* \* \*